(12) United States Patent
Lloyd et al.

(10) Patent No.: US 10,359,380 B2
(45) Date of Patent: Jul. 23, 2019

(54) METHODS AND SYSTEMS FOR MEASURING MELTING TEMPERATURES

(71) Applicant: C.Y. O'CONNOR ERADE VILLAGE FOUNDATION INC., Piara Waters (AU)

(72) Inventors: Sally Stevens Lloyd, West Australia (AU); Roger Letts Dawkins, West Australia (AU)

(73) Assignee: C.Y. O'CONNOR ERADE VILLAGE FOUNDATION INC., Piara Waters (AU)

( * ) Notice: Subject to any disclaimer, the term of this patent is extended or adjusted under 35 U.S.C. 154(b) by 64 days.

(21) Appl. No.: 15/120,823

(22) PCT Filed: Feb. 25, 2015

(86) PCT No.: PCT/IB2015/000876
§ 371 (c)(1),
(2) Date: Aug. 23, 2016

(87) PCT Pub. No.: WO2015/128737
PCT Pub. Date: Sep. 3, 2015

(65) Prior Publication Data
US 2016/0363547 A1    Dec. 15, 2016

(30) Foreign Application Priority Data
Feb. 25, 2014   (AU) ................. 2014900603

(51) Int. Cl.
*G01N 25/04* (2006.01)
*G01N 33/03* (2006.01)

(52) U.S. Cl.
CPC ............ *G01N 25/04* (2013.01); *G01N 33/03* (2013.01)

(58) Field of Classification Search
CPC ............................ G01N 25/04; G01N 33/03
See application file for complete search history.

(56) References Cited

U.S. PATENT DOCUMENTS

| 2,741,099 A | 4/1956 | Beane |
| 4,465,703 A * | 8/1984 | Jasko ............ C11B 7/0008 426/607 |

(Continued)

FOREIGN PATENT DOCUMENTS

EP    0601964    6/1994

OTHER PUBLICATIONS

"AOCS Official Method Cc 3-25," AOCS, retrieved from https://www.aocs.org/attain-lab-servies/methods/methods/search-results?method=111508&keywords=, retrieved on Sep. 27, 2016, 1 page, abstract.

(Continued)

*Primary Examiner* — Lisa M Caputo
*Assistant Examiner* — Philip L Cotey
(74) *Attorney, Agent, or Firm* — Sheridan Ross P.C.

(57) ABSTRACT

The invention relates to methods and systems for measuring the melting point of a material. The method and systems of the invention may reduce the time required to determine the melting point of one or more samples. Furthermore, the methods and systems of the invention result in an accurate and precise measurement of the melting temperature. Thus, the method and system of the invention are preferred over current methods for measuring the melting point.

20 Claims, 7 Drawing Sheets

(56) References Cited

U.S. PATENT DOCUMENTS

| | | | | |
|---|---|---|---|---|
| 4,522,786 | A | 6/1985 | Ebersole | |
| 4,933,525 | A | 6/1990 | St. Phillips | |
| 5,576,197 | A * | 11/1996 | Arnold | B01L 3/50825 208/20 |
| 5,779,946 | A * | 7/1998 | Bogue | A23G 3/10 264/40.6 |
| 6,302,134 | B1 * | 10/2001 | Kellogg | B01F 13/0059 137/251.1 |
| 6,432,718 | B1 * | 8/2002 | Umezawa | G01N 33/206 148/508 |
| 6,833,536 | B2 * | 12/2004 | Shigeura | B01J 19/0093 219/385 |
| 7,498,175 | B2 * | 3/2009 | Cole | B01D 1/0029 159/44 |
| 8,313,906 | B2 * | 11/2012 | Cao | C12N 15/1017 435/283.1 |
| 8,701,587 | B2 | 4/2014 | Park | |
| 9,568,478 | B2 * | 2/2017 | Egry | G01N 33/582 |
| 2004/0120381 | A1 * | 6/2004 | Matsuo | G01K 11/06 374/10 |
| 2005/0241491 | A1 * | 11/2005 | Sollich | G01N 25/04 99/353 |
| 2009/0190626 | A1 * | 7/2009 | Bradley | G01N 25/04 374/16 |
| 2010/0112168 | A1 * | 5/2010 | Garwood | A22C 17/00 426/480 |
| 2010/0256004 | A1 * | 10/2010 | Tashiro | B01J 19/0046 506/9 |
| 2010/0280789 | A1 * | 11/2010 | Kubo | G01N 25/04 702/130 |
| 2011/0093207 | A1 * | 4/2011 | Ingber | B04B 9/14 702/19 |
| 2011/0271895 | A1 * | 11/2011 | Park | G01K 3/04 116/216 |
| 2013/0218476 | A1 * | 8/2013 | Cheng | G06F 19/10 702/19 |
| 2013/0338928 | A1 * | 12/2013 | Mustola | G06F 19/24 702/19 |
| 2014/0038170 | A1 * | 2/2014 | Opalsky | G01N 25/04 435/5 |
| 2014/0147883 | A1 * | 5/2014 | Prins | G01N 1/2813 435/40.5 |
| 2016/0040213 | A1 * | 2/2016 | Ludowise | B01L 3/5027 435/287.2 |

OTHER PUBLICATIONS

"AOCS Official Method Cc 3b-92," AOCS, retrieved from https://www.aocs.org/attain-lab-services/methods/search-results?method=111509&keywords=, retrieved on Sep. 27, 2017, 1 page, abstract.

International Search Report for the International (PCT) Application No. PCT/IB15/00876, dated Sep. 9, 2015, 6 pages.

Written Opinion for International (PCT) Application No. PCT/IB15/00876, dated Sep. 9, 2015, 6 pages.

International Preliminary Report on Patentability for International (PCT) Application No. PCT/IB15/00876, dated Aug. 30, 2016, 7 pages.

Official Action for Australia Patent Application No. 2015221851, dated Nov. 5, 2018 3 pages.

* cited by examiner

METHODS AND SYSTEMS FOR MEASURING MELTING TEMPERATURES

CROSS REFERENCE TO RELATED APPLICATION

This application is a national stage application under 35 U.S.C. 371 of PCT Application No. PCT/IB2015/000876 having an international filing date of Feb. 25, 2015, which designated the United States, which PCT application claimed the benefit of Australian Application Serial No. 2014900603, filed Feb. 28, 2014, both of which are incorporated by reference in their entirety.

FIELD OF THE INVENTION

This invention relates to a method and system for measuring the melting temperature of a material.

BACKGROUND

Pure substances melt at a precise temperature. Complex mixtures such as edible fats and oils have a temperature range over which melting occurs. It is common to measure the lowest temperature at which the mixture behaves as a liquid and designate that temperature as its melting point.

This invention has been made in the context of determining the melting point of materials such as animal fats. Animal fats are mixtures of long chain fatty acids largely in the form of triglycerides. The melting point of a particular fat is largely determined by the proportion of saturated, monounsaturated and polyunsaturated fatty acids (SFAs, MUFAs and PUFAs, respectively) and the carbon chain length. The greater the proportion of SFAs, the higher the melting point of the particular fat. The shorter the fatty acid chains, the lower the melting point.

The type of fat in the diet is as important as the quantity for maintaining good health. Diets that replace SFA with MUFA or PUFA are similar to or better than diets that replace SFA with carbohydrates. These effects can be seen in fasting glucose and cholesterol profile and on coronary heart disease. While there has been a substantial public health effort in many countries to reduce the proportion of SFAs in diets, this has been largely focused on processed foods and reduction in consumption of animal fats. Hitherto there has been little recognition of the substantial variations in the SFA component in meat within and between species and under different animal production systems. Furthermore, increased MUFA content has been linked to better taste and texture of meat. Interest is growing in improving the MUFA content of meat and other meats. The effect of MUFA and PUFA content on palatability and health is associated with their lower melting points ($T_M$). Even within the SFA, lauric acid has a lower $T_M$ than stearic or palmitic acid and a better effect on the ratio of total cholesterol to high-density lipoprotein cholesterol.

Fat melting point is expected to have a growing role as a simple indicator of the fatty acid components and hence the health and palatability characteristics of meat.

Currently there are several methods for measuring the $T_M$ of fat, of which the most commonly used is the slip point or open capillary method (American Oil Chemists' Society official method Cc 3b-92; AOCS, 1998), the softening point (American Oil Chemists' Society official method Cc 3-25; AOCS, 1998), the point at which the fat becomes clear (American Oil Chemists' Society official method Cc 1-25; AOCS, 1998), the dropping point (American Oil Chemists' Society official method Cc 18-80; AOCS, 1998), and differential scanning calorimetry (AOCS, 1998; Nassu and Gonçalves, 1999). Since animal fats are mixtures, their melting is a gradual process and the different definitions of the $T_M$ in the various methods make it difficult to compare results (Nassu and Gonçalves, 1999). The slip point is the most commonly used $T_M$ measure for fats in food production. Other methods are less commonly used because they are more cumbersome, expensive, or inaccurate. Furthermore, since fats are mixtures, their melting is a gradual process and the different definitions of the melting point in the various methods make it difficult to compare results.

All these methods lack the capacity for real-time multiple sample testing. Therefore, an accurate $T_M$ assay suitable for testing fat from large numbers of animals is desirable.

SUMMARY

An aspect of the invention is a method to determine a melting point of a test material in a container. The test material and a detection material are in the container, and the detection material is located above the test material in the container at a starting temperature. The container is heated, and the test material and the detection material invert positions in the container once the test material melts. The change in the relative position of the test material and the detection material is detected and the temperature is recorded.

In some embodiments of the invention, the test material in the liquid state, and the detection material are immiscible. The test material may be less dense than the detection material over the test temperature range (between the starting temperature and the recorded temperature). The test material, detection material and container may be heated in a chamber. The detection material may remain a liquid over a testing temperature range.

The test materials may be fat, a cosmetic, a hydrocarbon, and a wax. In some embodiments, the test material may be an animal fat. The detection material may be an aqueous solution. The detection material may include a dye, such as a fluorescent dye. At least one optical property of the test material in its solid state may be different from the same optical property of the detection material.

The detection step may include detecting an optical property of the detection material. The optical property may be fluorescence, absorbance, reflectance, translucence, scatter, specific rotation or refractive index. The detection step and/or the recording step may be automated.

Another aspect of the invention is a system for measuring the melting point of a material. The system includes a controlled area configured to receive a container, and a temperature control element. The temperature control element is adjacent to the controlled area and configured to provide heat to the controlled area and at least a portion of the container. The system also includes a temperature sensor to measure a temperature of the controlled area and at least one detector. The detector provides a signal when a detection condition is met. The system also includes a controller to provide a control signal to the heating element and alter the temperature associated with the controlled area. The controller also receives the signal from the detector and records the temperature associated with the control are when the signal is received.

In an embodiment of the invention, the temperature control element may cool the controlled area and at least a portion of the container. The detector in the system may be a photodetector and/or a photomultiplier. In some embodiments, the controller may be automated.

A further aspect of the invention is a method to determine a melting point of a fat in a container(s). The container(s) include the fat and an aqueous detection material. The aqueous detection material is located above the fat, which is a solid, in the container(s) at a starting temperature. The aqueous detection material includes a fluorescent dye that is soluble in an aqueous detection material. The method includes heating the container(s) and causing the fat in the container to invert positions with the aqueous detection material once the fat melts. A change in the positions of the fat and the aqueous detection material are detected because of a signal that corresponds with the dye in the aqueous detection material and the temperature is recorded. In some embodiments, the detection step and/or the recording step may be automated.

DETAILED DESCRIPTION

Figure 1A:
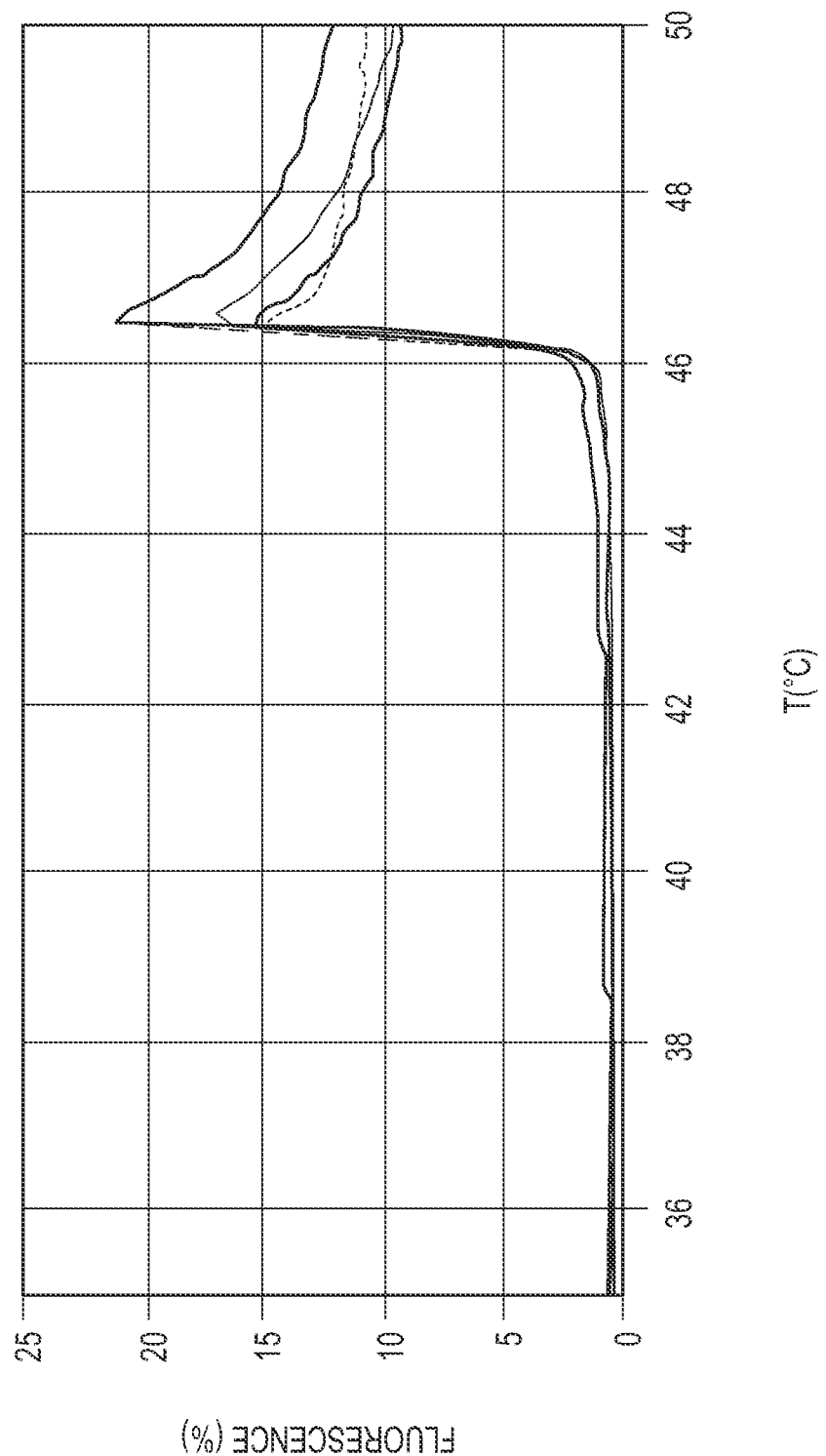
FIG. 1A illustrates fluorescence-temperature curves for 4 aliquots of rendered animal fat.

The invention relates to methods and systems for measuring the melting point of a material. The present invention provides a number of significant advantages over known methods of measuring the melting point of materials. As demonstrated below in the Examples section, the present invention achieves more accurate and consistent values of melting points of materials compared to, for example, the prior art slip method. In addition, the present invention can conveniently be automated and process large numbers of samples simultaneously. For example, existing systems for conducting polymerase chain reaction (PCR) can be adapted for use of the present invention to test multiple samples at the same time.

An aspect of the invention includes a method to determine the melting point of a test material. The method includes placing the test material into a container in a liquid form, where the test material is then solidified in the container. A detection material is placed into the container above the test material. The test material is heated to a temperature above its melting point. During the heating step, the fluidity of the test material is increased, and the detection material and the test material invert positions in the container. The temperature at which the inversion occurs is recorded to determine the melting point of the test material.

The test material in the liquid state and the detection material are immiscible. The detection material may be a liquid at an initial test temperature and may remain a liquid at the melting point of the test material. In some embodiments, the detection material may be selected so that it may remain as a liquid at temperatures exceeding the melting temperature and does not change from a liquid to a gas. Thus, in some embodiments, the boiling point of the detection material is greater than the melting point of the test material. The volume of the test material may be at least about 5% of the volume of the container. In some embodiments, the volume of the test material may be about 5% of the volume of the container, about 10% of the volume of the container, about 15% of the volume of the container, about 20% of the volume of the container, about 25% of the volume of the container, about 50% of the volume of the container, about 75% of the volume of the container, about 80% of the volume of the container, about 90% of the volume of the container, or about 95% of the volume of the container. The volume of the detection material may be at least about 5% of the volume of the container. In some embodiments, the volume of the detection material may be about 5% of the volume of the container, about 10% of the volume of the container, about 15% of the volume of the container, about 20% of the volume of the container, about 25% of the volume of the container, about 50% of the volume of the container, about 75% of the volume of the container, about 80% of the volume of the container, about 90% of the volume of the container, or about 95% of the volume of the container.

In some embodiments, the container may be a tube, a test tube, a capsule, a vessel, a vial, a PCR tube, or the like. The container may be configured to fit into a system for performing the test. Furthermore, in some embodiments, the container may be sealed after the test material and detection material are added to the container. The container may be sized so that the gravitational force in the container dominates capillary forces in the container. The material of the container can be such that it does not interfere with measurement of one or more optical properties of the test material and the detection material.

In some embodiments, the test material can be placed into the container by melting the test material to increase the fluidity of the test material prior to placing the test material into the container. The test material can return to a solid state as it is being placed into the container or after it has been placed into the container. In some embodiments the method may further include centrifuging the container with the test material in the container so that the test material is near the bottom of the test tube prior to placing the detection material into the test tube.

One skilled in the art would understand that the test temperature range will depend upon the melting point of the test material. The starting test temperature may be any temperature below the melting point of the test material. In some embodiments, the starting temperature may be between about 4° C. to about 50° C., or between about 10° C. to about 30° C. In some embodiments, the starting temperature may be about room temperature (approximately 25° C.). In some embodiments, the starting temperature may be about 4° C. The test material may be maintained at the starting temperature, with or without the detection material, for at least about 1 minute before the temperature may be increased. In some embodiments, the test material may be maintained at a below the melting point temperature, which may be the starting temperature, for between about 1 minute to about 24 hours. In some embodiments, the test material may be maintained at the temperature for about 30 minutes, about 1 hour, about 2 hours, about 5 hours, about 10 hours, about 12 hours, about 15 hours, about 20 hours or about 24 hours. The temperature may be increased over the test temperature range—from the starting temperature to the end temperature—where the melting point is within the test temperature range. The temperature of the test material, the container, or the system containing the container, test material and the detection material, may be increased incrementally. The temperature may be increased at a ramp rate between about 0.01° C./min to about 10° C./min. In some embodiments, the ramp rate may be about 0.01° C./min, about 0.1° C./min, about 0.5° C./min, about 1° C./min, about 1.5° C./min, about 2° C./min, about 5° C./min, about 7° C./min, or about 10° C./min. The ramp rate should be chosen so that the system evenly heats the test material within the container. In some embodiments, the temperature may be increased by between about 0.05° C. to about 1° C., then maintained at the temperature for between about 1 second to about 1 minute. In some embodiments, the temperature increase may be about 0.05° C., about 0.1° C., about 0.15° C., about 0.2° C., about 0.25° C., about 0.3° C., about 0.5° C., about 0.75° C., or about 1° C. In some embodiments, the temperature may be maintained between increments for between about 1 second, about 2 seconds, about 5 seconds, about 10 seconds, about 30 seconds, about 45 seconds, or about 60 seconds.

The melting temperature may be determined by detecting the temperature when the test material and the detection material invert positions in the container. The melting temperature may be measured directly or may be measured indirectly, for example by measuring the temperature of the system containing the container with the test material or by measuring another property. Determining when the test material and the detection material invert positions in the container can be achieved by detecting at least one optical signal from the detection material if the test material and the detection material have different values of at least one optical property. This difference may be evidenced while the test material is a solid, or liquid. The optical signal may be a fluorescence signal, an absorbance, a reflectance, a scatter, a translucence signal, a specific rotation, a refractive index or the like. In some embodiments, a material may be added to the detection material to change at least one optical property of the detection material. At the starting temperature, the optical property of the test material may be monitored. After the inversion, the optical property of the detection material may be monitored. In some embodiments, the optical property may be monitored at the bottom of the container. In some embodiments, the detection of the inversion of the test material and the detection material may be automated, as may the recording of the temperature when the materials invert positions. Furthermore, multiple test material samples may be tested simultaneously, or in quick succession to decrease the time required to receive melting point temperatures on several samples.

In some embodiments, the test material may be a fat, such as an animal fat or a vegetable fat. The test material may be from, for example, an animal for consumption to evaluate the fat composition of the animal. The method may be used to determine the melting temperature of fat from a particular animal. The animal may be a cow, a chicken, a pig, a bison, a lamb, a goat, or other animal that is consumed. In some embodiments, the test material may be a cosmetic. The cosmetic material may be used for base, lipstick, lip balm, mascara, eye shadow, blush, eyeliner, concealer, primer, lip gloss, foundation, powders, creams or the like. The test material may be soap, lotions, or creams. The test material may also be a hydrocarbon, mineral oil, wax, plastic, polymer or the like.

The detection material may be any suitable material. In some embodiments, the detection material may be an aqueous solution. The detection material may further include an optical component, which may be added to the detection material in order to produce at least one optical property that is different from the same optical property of the test material. The optical component may be dissolved or suspended in the detection material. By way of example, the optical component may be a dye, such as a fluorescent dye, an absorbance dye, a reflecting dye, a translucence dye, a colloid (which may increase scatter in a signal), a chiral substance (which may increase specific rotation) and combinations thereof. Between about 0.0000008 wt % of the total solution to about 40 wt. % of the total solution of the aqueous solution with the dye may be the dye. In some embodiments, the weight percent of the dye in the total solution may be about 0.0001 wt %, about 0.01 wt %, about 0.1 wt %, about 1 wt %, about 5 wt %, about 10 wt %, about 20 wt %, about 30 wt %, or about 40 wt %. In some embodiments, the optical signal may correspond to the optical material added to the detection material.

In some embodiments, the density of the detection material is greater than the density of the test material over the testing temperature range. The density of the detection material may be controlled so that it is greater than the density of the test material. A density altering material may be added to the detection material, such as a material soluble in the detection material. Suitable density altering materials include, but are not limited to, salt, sugar, acid, base, proteins and the like. Preferably, the density altering material may be salt, and the salt may be any suitable salts, including but not limited to, $NaCl$, $KCl$, $NaBr$, $Na_2SO_4$, $K_2SO_4$, $KI$, $CuSO_4$, $CaCl_2$, $KMnO_4$, $CH_3COONa$, $(CH_3COO)_2Ca$, $NaNO_3$, $KNO_3$, $Al(NO_3)_3$, $Al_2(SO_4)_3$, $MgSO_4$, $Na\ HCO_2$, $MgCl_2$ $NaCO_3$ and combinations thereof.

The method can be conducted to occur in a chamber. The heating step and/or detection step may occur in the chamber. In some embodiments, the chamber may be part of a system used for polymerase chain reaction (PCR). The chamber may hold a single sample, or may hold multiple samples. The chamber may be able to heat and detect at least one sample at a time. The chamber may heat samples within the chamber evenly and consistently. The chamber may include a sensor to measure the temperature within the chamber and/or to measure the temperature of the samples. In some embodiments, a centripetal force may be applied to the container, such that gravitational forces and centripetal forces may cause the inversion of the test material and the detection material.

An aspect of the invention is a system for detecting the melting point of a material. The system includes a controlled area configured to receive a container, a heating element disposed adjacent to the controlled area and configured to provide heat to the controlled area and at least a portion of the container. The system also includes a temperature sensor configured to measure a temperature associated with the controlled area and a detector configured to provide a signal when a detection condition is met. The system also includes a controller configured to provide a control signal to the heating element and alter the temperature associated with the controlled area, receive the signal from the detector, and record the temperature associated with the controlled area at a time the signal is received.

The system may include a processor. The processor may comprise a general purpose programmable processor or controller for executing application programming or instructions. The processor may, optionally, include multiple processor cores, and/or implement multiple virtual processors. Additionally or alternatively, the processor may include multiple physical processors. As a particular example, the processor may comprise a specially configured application specific integrated circuit (ASIC) or other integrated circuit, a digital signal processor, a controller, a hardwired electronic or logic circuit, a programmable logic device or gate array, a special purpose computer, or the like. The processor generally functions to run programming code or instructions implementing various functions of the measuring and recording system and/or the components of the measuring and recording system.

Optionally, the systems and methods of this disclosure can be implemented in conjunction with a special purpose computer, a programmed microprocessor or microcontroller and peripheral integrated circuit element(s), a programmable logic controller (PLC), an ASIC or other integrated circuit, a digital signal processor, a hardwired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, Intel® Core® i5-4670K and i7-4770K 22 nm Haswell, Intel® Core® i5-3570K 22 nm Ivy Bridge, AMD®, FX-4300, FX-6300, and FX-8350 32 nm Vishera, AMD®, Kaveri processors, ARM® Cortex™-M processors, ARM® Cortex-A and ARM926EJ-S™ processors, other industry-equivalent controllers, and other industry-equivalent processors.

Embodiments include a system, comprising: a controlled area configured to receive a container; a heating and/or cooling element disposed adjacent to the controlled area and configured to provide heat to the controlled area and at least a portion of the received container; a temperature sensor configured to measure a temperature associated with the controlled area; a detector configured to provide a signal when a detection condition is met; and a controller configured to provide a control signal to the heating element and alter the temperature associated with the controlled area, receive the signal from the detector, and record the temperature associated with the controlled area at a time the signal is received. Aspects of the above system include wherein the container includes a volume configured to receive a test material and a detection material therein. Aspects of the above system include wherein the container is further configured to contain the test material in a first location and the detection material in a second location, wherein the first location is beneath the second location. Aspects of the above system include wherein the detection condition corresponds to a location inversion of the test material and the detection material such that the detection material is in the first location and the test material is in the second location. Aspects of the above system include wherein the container is a test tube. Aspects of the above system include wherein the detector is at least one of a photodetector (including photodiodes, photomultipliers or charge-coupled devices), and optical sensor. Aspects of the above system include wherein the temperature sensor is at least one of a thermocouple, thermometer, infrared sensor, thermistor, and thermal radiation detector. Aspects of the above system include wherein the heating element is at least one of a radiative heating element, induction heating element, flame, electromagnetic radiation source, infrared heater, heat lamp, Peltier element, and chemical heat source. Aspects of the above system include wherein the controlled area is a chamber.

In some embodiments, the container includes a volume configured to receive a test material and a detection material. The container may be configured to contain the test material in a first location and the detection material in a second location, wherein the first location is beneath the second location. In some embodiments, the container may be a tube, a test tube, a capsule, a vessel, a vial, a 100 micro liter PCR tube, or the like. The container may be configured to fit into the chamber. Furthermore, in some embodiments, the container may be sealed after the test material and detection material are added to the container. The container may be sized so that the gravitational force in the container may dominate capillary forces in the container. The material of the container may be chosen such that it does not interfere with at least one optical measurement of the test material and the detection material.

In some embodiments, the chamber may include a holding element configured to put a centripetal force on the container within the chamber. In some embodiments, a centripetal force may be applied to the container, such that gravitational forces and centripetal forces may cause the inversion of the location of the test material and the detection material.

In some embodiments, the detection condition may correspond to a location inversion of the test material and the detection material such that the detection material is in the first location and the test material is in the second location. The detector may be at least one of a photodetector, photomultiplier, or an optical sensor. The melting temperature may correspond to the detection condition. The melting temperature may be measured directly or may be measured indirectly, for example by measuring the temperature of the chamber containing the container with the test material or by measuring another property. The detector may detect at least one optical signal. At least one optical signal in the detection material may be detected when the test material and the detection material invert positions in the container. The test material and detection material may have different values of at least one optical property. This difference may be evidenced while the test material is a solid, or liquid. The optical signal may be a fluorescence signal, an absorbance, a reflectance, a scatter, a translucence signal, a specific rotation, a refractive index, combinations thereof or the like. In some embodiments, a material may be added to the detection material to change at least one optical property of the detection material. At the starting temperature, the detection property of the test material may be monitored. After the inversion, the detection property of the detection material may be monitored, indicating the detection condition. In some embodiments, the detection condition may be monitored at the bottom of the container.

The temperature sensor may be any suitable temperature sensor. In some embodiments, the temperature sensor may be one or more of a thermocouple, thermometer, infrared sensor, thermistor, or thermal radiation detector. The temperature sensor may be arranged at least partially within the chamber or in proximity to the chamber. In one embodiment, the temperature sensor may be configured to measure a temperature of the test material, container, chamber, etc., and/or combinations thereof. In some embodiments, the temperature sensor may be configured to communicate a measured temperature to a controller of the system. This communication may be made via wired or wireless communications.

The heating element may be positioned or otherwise arranged to provide heat to one or more portions of the chamber. In some embodiments, the heating element may be at least partially disposed within the chamber. In any event, the heating element may be configured to provide heat to a test material in the chamber and/or a container. The heating element in the chamber may be any suitable element. By way of example, the heating element may be at least one of a radiative heating element, an induction heating element, a flame, an electromagnetic radiation source, an infrared heater, a heat lamp, or a chemical heat source. The heating element in the chamber may operate from a starting test temperature to an end temperature (the temperature test range), such that the starting temperature may be any temperature below the melting point of the test material. In some embodiments, the starting temperature of the test may be between about 4° C. to about 50° C., or between about 10° C. to about 30° C. In some embodiments, the starting temperature may be about room temperature (approximately 25° C.). In some embodiments, the starting temperature may be about 4° C. The test material may be maintained at the starting temperature, with or without the detection material, for at least about 15 minutes before the temperature may be increased. In some embodiments, the test material may be maintained at or below the melting point temperature, which may be the starting temperature, for between about 15 minutes to about 24 hours. The temperature may be increased over the test temperature range—from the starting temperature to the end temperature—where the melting point is within the test temperature range. The heat output of the heating element may be increased incrementally. The heating element may increase the temperature of the chamber at a ramp rate between about 0.01° C./min to about 10° C./min. In some embodiments, the ramp rate may be about 0.01° C./min, about 0.1° C./min, about 0.5° C./min, about 1° C./min, about 1.5° C./min, about 2° C./min, about 5° C./min, about 7° C./min, or about 10° C./min. The ramp rate should be chosen so that the system evenly heats the test material within the container.

In some embodiments, a control signal provided via a controller, or heat controller, of the system may control the heat output of the heating element. In one embodiment, the control signal provided by the controller may control an amount of energy, voltage, or power, provided to the heating element. In another embodiment, the control signal provided by the controller may control a valve to a power source for the heating element. Additionally or alternatively, the controller may control the amount of time that a power signal is provided to the heating element. In any event, the controller may provide a heat output profile for the heating element. This heat output profile may include specific energy output for the heating element over time. By way of example, the heat output profile may include the ramp rate as disclosed herein. In some embodiments, the heating element may be controlled, via the controller, in response to receiving a measured temperature from the temperature sensor. For example, the controller may provide a control signal configured to activate the heating element until a particular temperature is measured. In one embodiment, when the particular temperature is measured the control signal may be ceased. This particular temperature may be configured to account for overshoot, undershoot, and/or other aspect of proportional control. As can be appreciated, the controller may be configured to selectively provide and/or cease an activation control signal such that the heating element can be turned on and off, for example, to follow a particular temperature ramp or profile.

Figure 6:
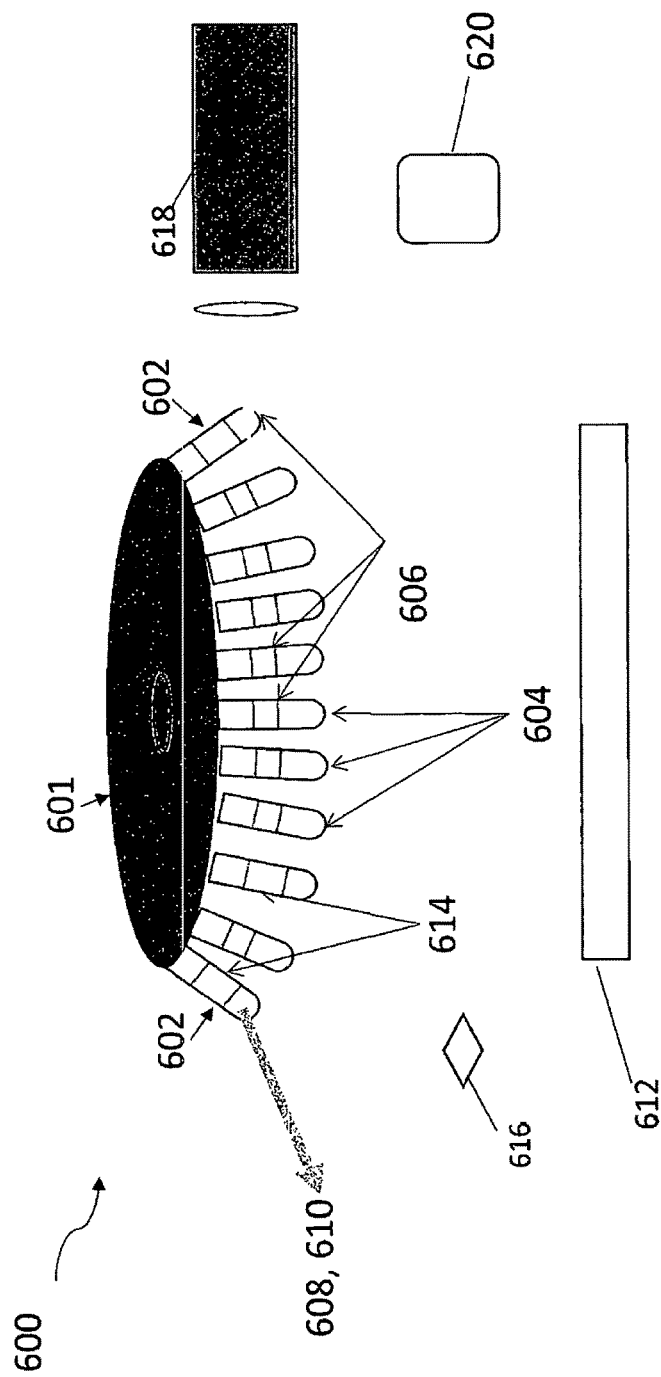
FIG. 6 illustrates an embodiment of the system of the invention.

FIG. 6 illustrates an embodiment of the system 600. The system includes a holding element 601, which holds a plurality of containers 602. The container 602 comprises a solid fat sample 604 and a detection material 606. Once the centrifugal force 608, gravitational force 610 (the direction of the sum of the forces illustrated by the arrow in FIG. 6) and heat from the heating element 612 are applied, the solid fat sample 604 melts and inverts position 614. The temperature sensor 616 measures the temperature in the system 600. The detector 618 provides a signal when a detection condition is met. The controller 620 can provide a signal to the heating element 612 to adjust the temperature, receive a signal from the detector 618 and record a temperature from the temperature sensor 616 when a detection condition is met.

EXAMPLES

Equipment and Setup

The Rotor-Gene Q was developed for PCR amplification and characterization of the products based on the temperature at which the double stranded DNA denatures into single stranded DNA. The amplification and analysis requires rapid and precise temperature control, centrifugation, and real-time fluorescence detection which are exactly the components required to perform a unique measurement of fat $T_M$.

Twenty microliters of melted fat samples were transferred into 0.1-mL tubes. The tubes were then centrifuged at 9.8×g and at 75° C. for 2 min to collect the fat at the base of the tubes. The fat was solidified at 4° C. for at least 12 h. Then, 10 µL of 26 µM fluorescein dye in deionized distilled water was added to form a layer above the fat. The samples were conditioned at 25° C. for 90 s in the Rotor-Gene Q assembly. During the conditioning step, the photomultiplier gain was optimized using a tube loaded with dye only, which provided a reference fluorescence level.

Fluorescence detection in the Rotor-Gene Q is focused on the base of each tube. At the start of a run, the dye was above the fat and the fluorescence detection was low (see FIG. 1A for temperatures below 45° C.). During the run, the temperature increased in 0.1° C. steps with a rest time of 2 s at each step. At the $T_M$ transition there was a sharp increase in fluorescence (FIG. 1A; at about 46° C.).

Gravitational and centrifugal forces pulled the dye down, through the liquefied fat, into the field of view of the detector, increasing the fluorescence signal. The inversion occurred because fat is less dense than the aqueous dye.

The $T_M$ is the temperature at which the fluorescence signal changes most rapidly. This temperature, at the peak in the derivative of fluorescence with respect to temperature (illustrated in FIG. 1b) is calculated automatically by the Rotor-Gene Q software.

Example 1

The present method was compared against the slip point measurement test. The three standards were used during the experiments:
1. A sample of adipose tissue taken from the skirt fat of a Simmental steer slaughtered at 12 months. The samples were heated to about 90° C. for about 12 hours and separated the melted fat from the water and solids by pipette.
2. Supafry (Goodman Fielder, NSW, Australia) is a commercially available rendered animal fat with a saturated fat content of 48% (wt/wt).
3. Allowrie Ghee (Fonterra, VIC, Australia) is clarified butter and has a saturated fat content of 66% (wt/wt).

Aliquots of each standard were stored at 4° C. Fat samples were taken from 67 full-blood Wagyu steer carcasses slaughtered at an average age of 26.3 months (SD=1.7) after an average of 320 days on feed (SD=14). Approximately 1 mL of adipose tissue was scraped from the subcutaneous fat layer between the 10th and 11th rib of each carcass. To provide a comparison, the subcutaneous fat from the sirloins of 17 Simmental carcasses were sampled. These were slaughtered at between 9 and 14 months, after 36 to 87 days on feed. The carcass samples were heated, to extract melted fat for $T_M$ measurements.

Slip Point Measurements

The slip point temperature was measured for each standard. First, melted fat was drawn into a glass capillary tube with an internal diameter of 1 mm to form a 1-cm column. The fat solidified in the capillary tubes while stored at 4° C. for at least 12 h. The position of the top of the fat column was marked on the capillary tubes, which were then attached to a thermometer marked in 1° C. divisions.

The thermometer was held in a beaker of water, which was heated gradually from 20 to 50° C. at 1° C./min with the top of the fat column below the surface of the water. The temperature at which the fat column rose was recorded as the slip point. Four slip points were measured for each standard. The results are shown in Table 1.

TABLE 1

| Sample | $T_m$ (° C.) | | |
|---|---|---|---|
| | Ghee | Skirt | Supafry |
| Test 1 | 32.0 | 40.5 | 45.5 |
| Test 2 | 32.5 | 40.0 | 45.0 |
| Test 3 | 33.0 | 40.0 | 45.0 |
| Test 4 | 32.0 | 38.0 | 45.0 |
| Mean | 32.4 | 39.6 | 45.1 |
| Standard Deviation | 0.5 | 1.1 | 0.3 |

The Method of the Invention

Table 2 shows the Rotor-Gene Q $T_M$ measurements of 7 aliquots of 3 different types of animal fat over 2 runs. Variation in $T_M$ measurements on duplicated samples within a run was very low. The variation between duplicates was small both within a run (average intra-assay SD of 0.08° C.) and between runs (average interassay SD of 0.10° C.). The assay was accurate over the range about 35 to 47° C.

TABLE 2

| Run | Sample | $T_m$ (° C.) | | |
|---|---|---|---|---|
| | | Ghee | Skirt | Supafry |
| 1 | Aliquot 1 | 35.42 | 40.90 | 46.32 |
| | Aliquot 2 | 35.40 | 41.07 | 46.25 |
| | Aliquot 3 | 35.43 | 41.17 | 46.35 |
| | Aliquot 4 | 35.52 | 41.40 | 46.28 |
| | Mean | 35.44 | 41.14 | 46.30 |
| | Standard Deviation | 0.05 | 0.21 | 0.04 |
| 2 | Aliquot 1 | 35.43 | 41.27 | 46.37 |
| | Aliquot 2 | 35.43 | 41.35 | 46.42 |
| | Aliquot 3 | 35.52 | 41.40 | 46.33 |
| | Mean | 35.46 | 41.34 | 46.37 |
| | Standard Deviation | 0.05 | 0.07 | 0.05 |

Figure 1B:
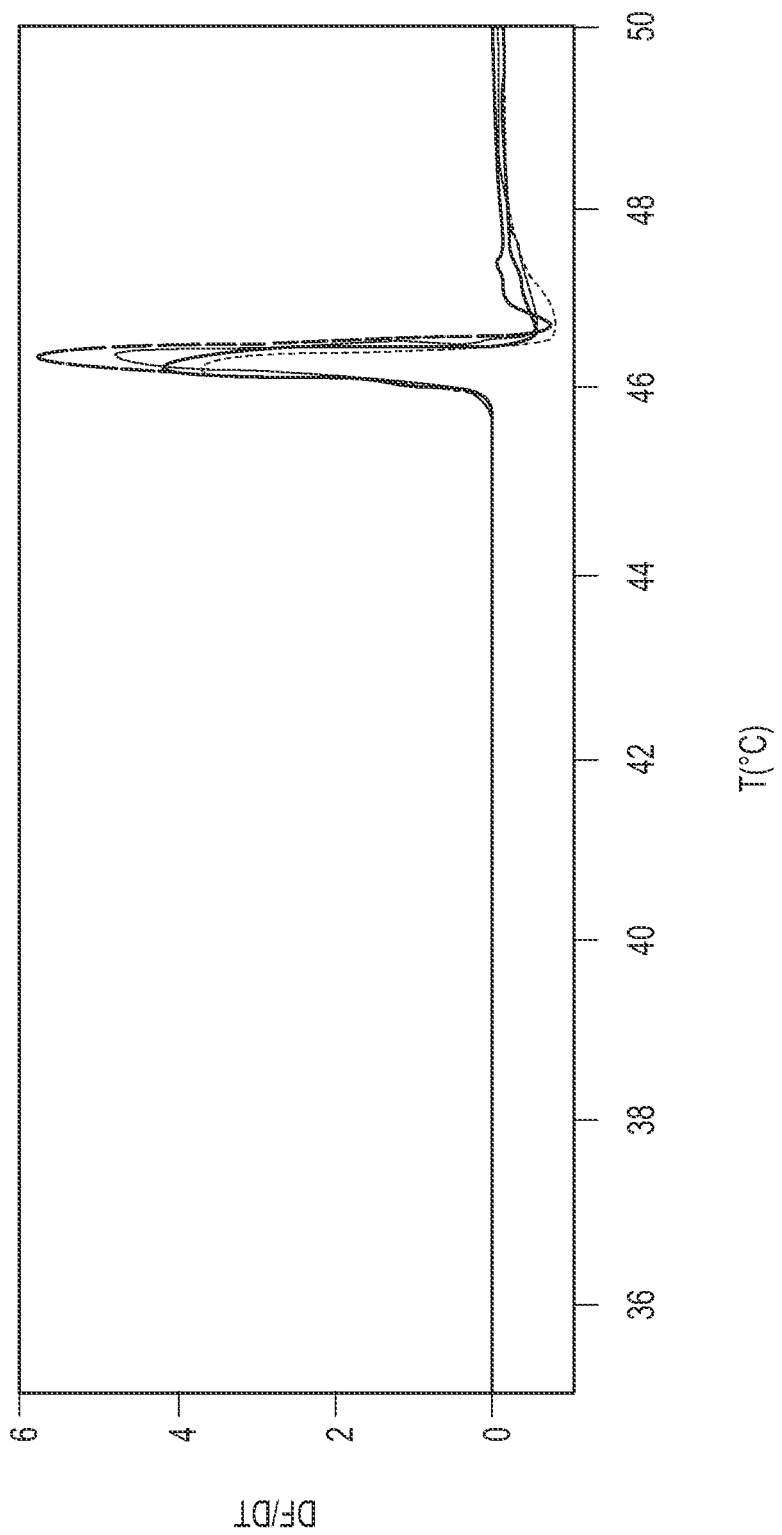
FIG. 1B illustrates the derivative of fluorescence as a function of with respect to temperature (dF/dT) as a function of temperature.

FIG. 1A illustrates fluorescence-temperature curves for 4 aliquots of rendered animal fat. Fluorescence is measured in relative units as a percentage of the maximum (saturated) signal. FIG. 1B illustrates the derivative of fluorescence as a function of with respect to temperature (dF/dT) as a function of temperature.

Figure 2:
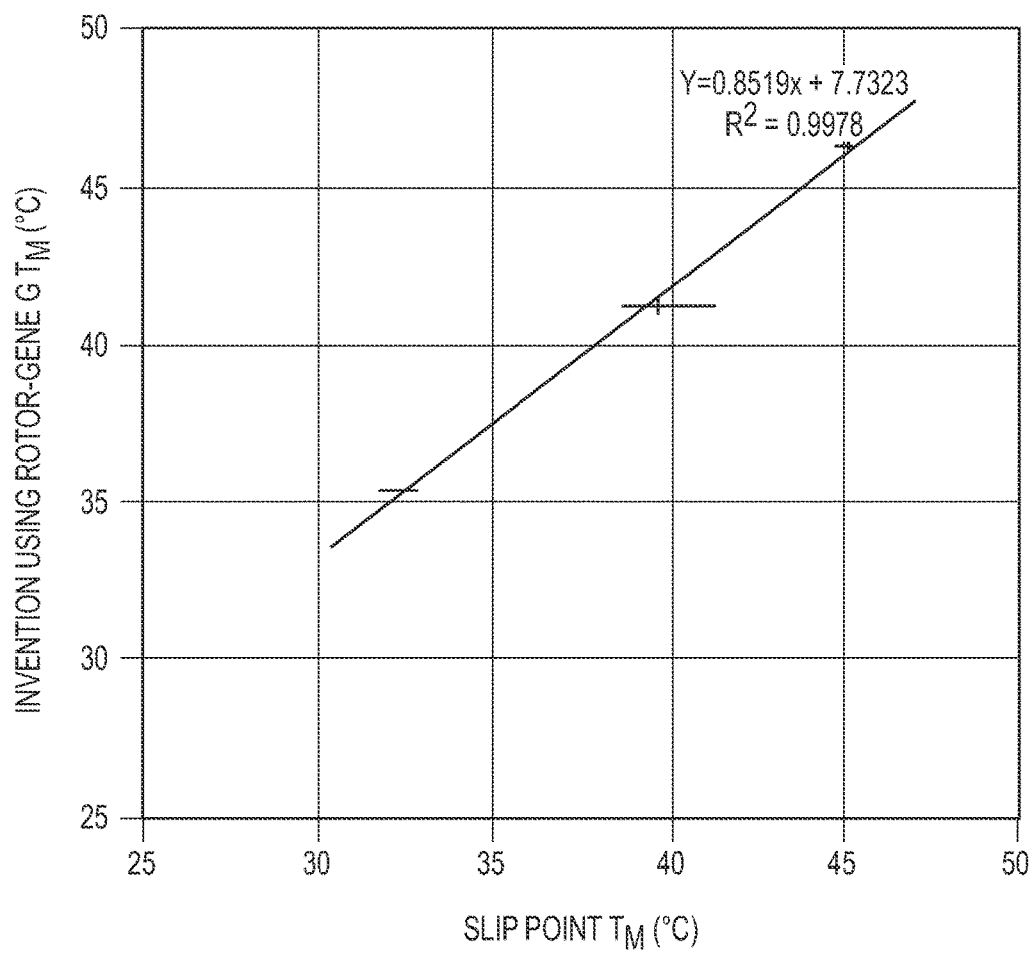
FIG. 2 illustrates a comparison of $T_M$ measurements using the invention with those using the slip point assay.

FIG. 2 illustrates a comparison of $T_M$ measurements using the invention with those using the slip point assay. The results are highly correlated but the slip point assay had more variability than the Rotor-Gene Q assay. Error bars show the large range of repeated measurements for the 4 slip point measurements compared to the small range of the 7 Rotor-Gene Q measurements. The Rotor-Gene Q $T_M$ assay can be used in place of the standard slip point assay for various animal fats. Linear conversion is possible with Rotor-Gene Q measurements 3.3° C. higher for slip points of 30 and 1.1° C. higher for slip points of 45° C. The slip point assay depends on observing fat solidified in a capillary tube rising when it melts. Slip point testing can be automated, to some extent, with purpose-designed machines. These improve the precision but not the throughput. The Melting Point M-565 (Buchi Laboratory Equipment, Flawil, Switzerland) can be used for slip point measurements of up to 3 samples at a time with a precision of 0.1° C.

Figure 3:
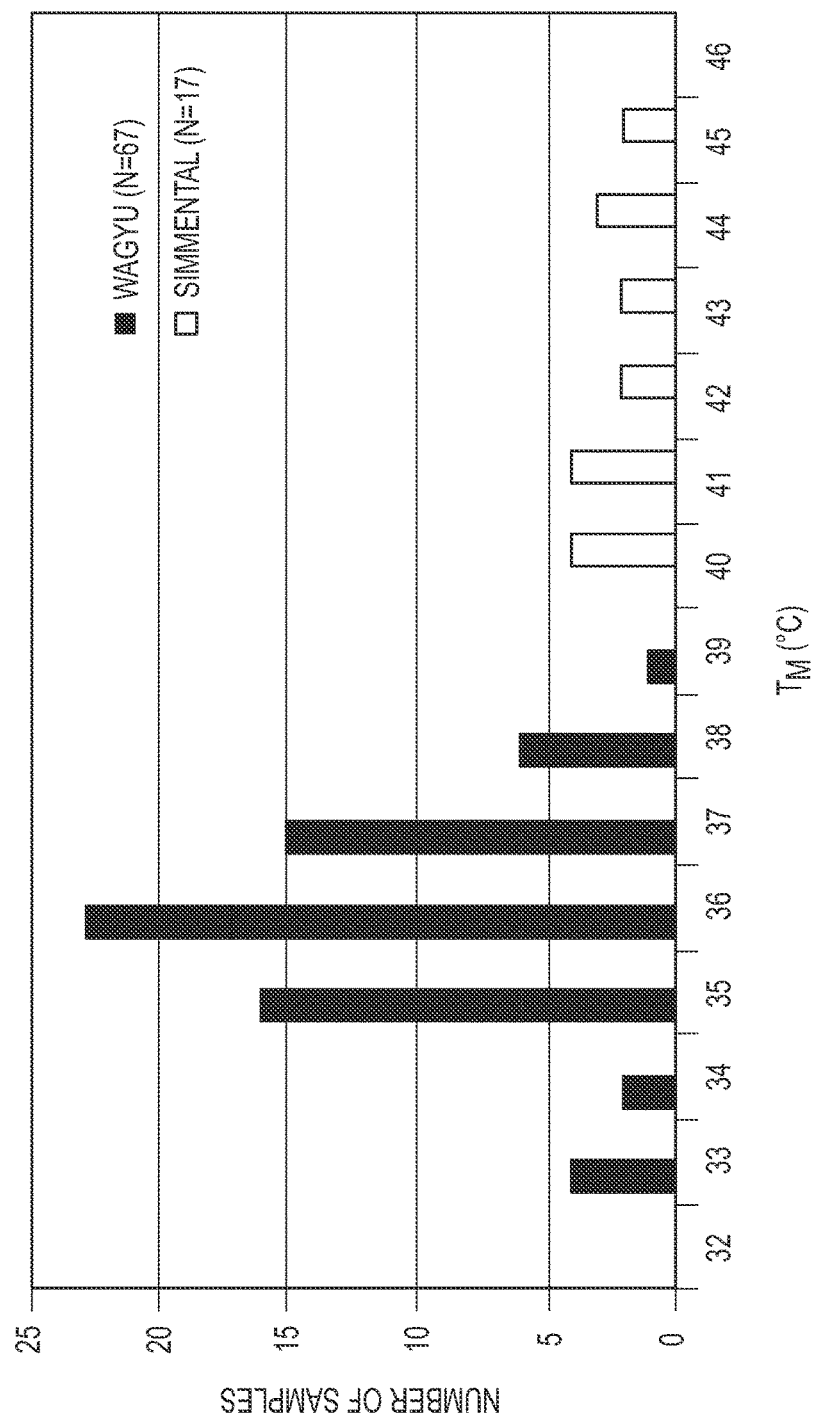
FIG. 3 illustrates melting points for a Wagyu and Simmental carcasses.

The method of the invention is more reliable and accurate and is capable of testing multiple samples at a time, depending upon the limitations of the system. By way of example only, the Rotor Gene Q assay allows up to 71 samples to be tested at a time. As an example of potential applications of this technique, the $T_M$ of subcutaneous fat from 67 Wagyu carcasses and 17 Simmental carcasses were measured. A single carcass was measured twice to give an indication of sampling variability, and the $T_M$ measurements differed by less than 0.2° C. The $T_M$ of the Wagyu samples ranged from 32.5 to 39.5° C. with an average of 36.0° C. and SD of 1.3° C. (as illustrated in FIG. 3). In contrast, the Simmental samples ranged from 39.6 to 45.1° C. with an average of 42.1° C. and SD of 1.7° C. The phase of a fatty acid at body temperature (37° C.) is known to be critical to its palatability and health effects. Of the 66 Wagyu carcasses sampled, 52 had fat that was liquid at 37° C. temperature while 14 had fat that still contained some solids at this critical temperature. All of the Simmental carcasses had $T_M$ well above body temperature. The lower $T_M$ of the fat samples from Wagyu is due to a combination of the softer fat from Wagyu and the longer time on feed. The variation of $T_M$ within full-blood Wagyu raised within the same environment is largely due to genetic variation. There is potential for genetic improvements in fat composition by selecting Wagyu breeding stock that produce low $T_M$ offspring.

Figure 4:
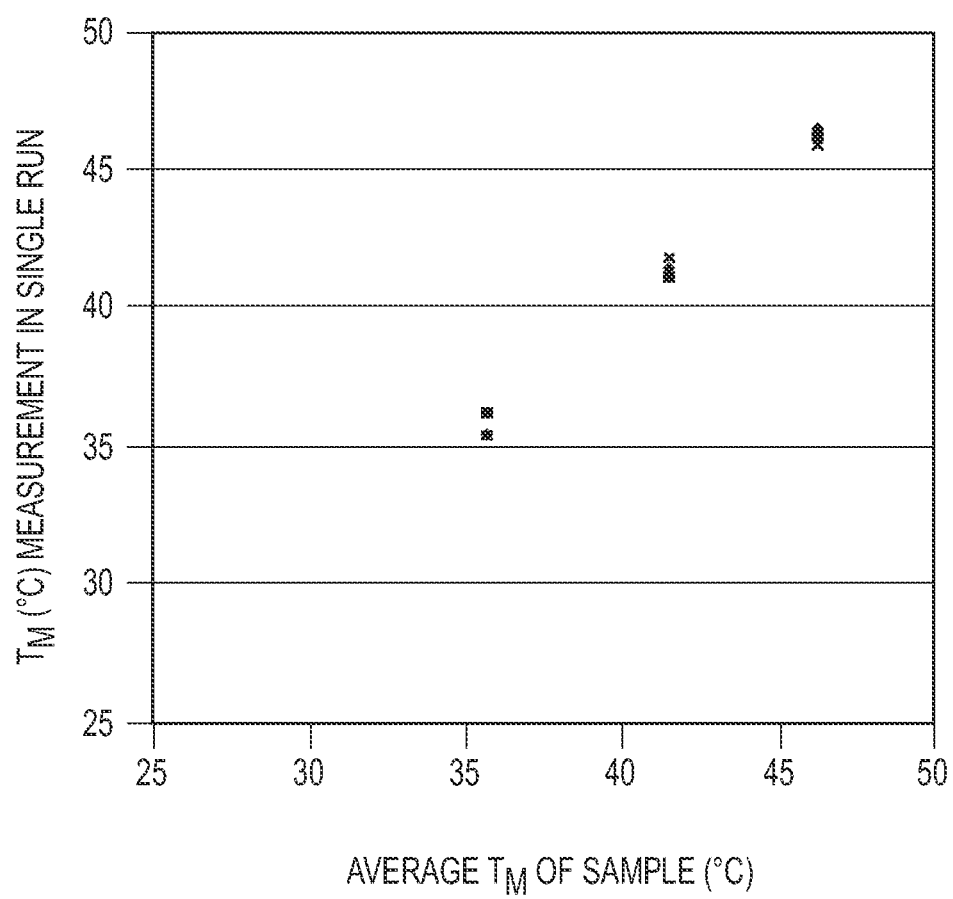
FIG. 4 illustrates the inter-assay variation for samples illustrating a minimal standard deviation.

FIG. 4 illustrates the inter-assay variation for samples. FIG. 4 illustrates an inter-assay standard deviation of 0.32° C.

Example 2

Comparison of Extraction Methods

In order to standardize the method of fat extraction from animal tissue, various methods have been compared. Lipid extraction methods may differ in their efficiency for extracting different lipid components based on degree of polarity. The extraction method chosen may affect the composition of the extracted fat and therefore its melting point.

Rendering Method:

Edible fats are often extracted from animal tissue by a simple application of heat, either with added water (wet rendering) or without (dry rendering). A version of this process was used to extract fat from samples of Wagyu meat. Approximately one gram of each sample was heated to 90° C. for at least 12 hours. The samples were than centrifuged to remove the solid tissue residue and the fat skimmed from the top.

Digestion Method:

A standard method of DNA extraction starts with digestion in an aqueous solution containing proteinase K at 56° C. for four hours. During this process the cell structure break down releasing both DNA and fat from the tissue. The DNA dissolves in the aqueous solution while the fat floats to the surface. Fat can be removed for melting point testing at this step without affecting the extraction of DNA from the aqueous position. This method of fat extraction from meat is preferred because it allows both DNA and fat to be easily extracted from one 0.5 gram meat sample.

Samples of meat from 12 Wagyu carcasses were used for this comparison. Each sample contained at least 20% intramuscular fat. Two grams of each sample were homogenised and then separated so that fat was extracted by both methods on each sample.

Figure 5:
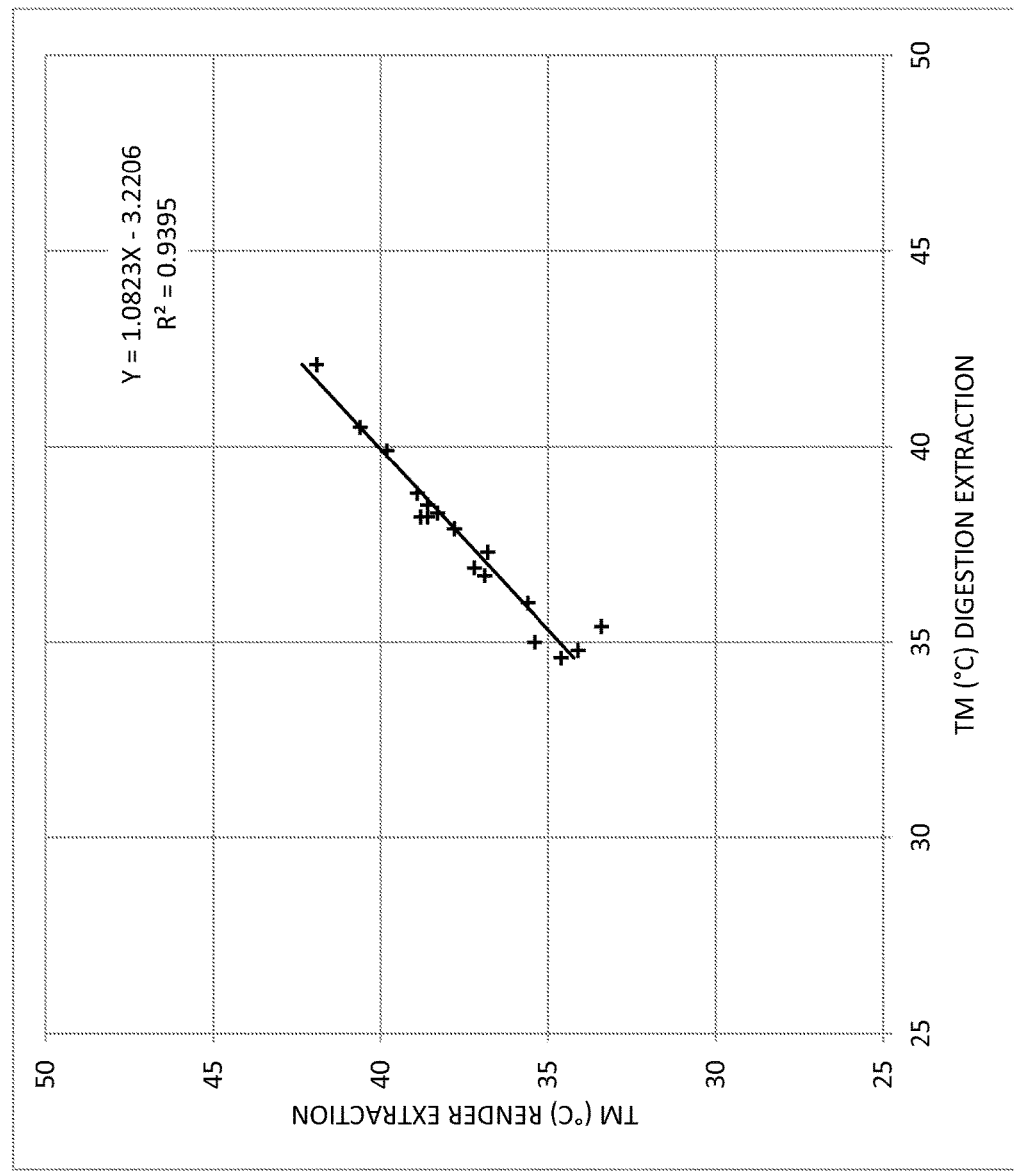
FIG. 5 illustrates the melting temperature of fat extracted by rendering compared with that of fat extracted by digestion.

The melting temperature of fat extracted by rendering was compared with that of fat extracted by digestion. The results are illustrated in FIG. 5. The results are closely correlated with slope close to one and intercept close to zero. This shows that the digestion method does not bias the melting point results and is a practical method for measuring melting point on samples where DNA extraction is also required The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A method to determine a melting point of a plurality of test materials in a plurality of containers, wherein a container of the plurality of containers each comprises a test material of the plurality of test materials and a detection material of a plurality of detection materials, and wherein the detection material of the plurality of detection materials is above the test material of the plurality of test materials at a starting temperature, comprising:
    heating the plurality of containers;
    applying a centripetal force to the plurality of containers, wherein the test material melts and the centripetal force cause inversion of the test material and the detection material in each of the plurality of containers;
    detecting a change in the relative position of the test material and the detection material in a container of the plurality of containers; and
    recording a temperature when the test material and the detection material in the container of the plurality of containers change relative position in the container.

2. The method of claim 1, wherein the test material, when in its liquid state, and the detection material are immiscible.

3. The method of claim 1, wherein the test material is less dense than the detection material over a temperature range between the starting temperature and the recorded temperature.

4. The method of claim 1, wherein the test material of the plurality of test materials is selected from the group consisting of a fat, a cosmetic, a hydrocarbon, and a wax.

5. The method of claim 1, wherein the test material is an animal fat.

6. The method of claim 1, wherein the detection material is an aqueous solution.

7. The method of claim 6, wherein the detection material further comprises a fluorescent dye.

8. The method of claim 1, wherein at least one optical property of the test material in its solid state is different from the same optical property of the detection material.

9. The method of claim 1, wherein the step of detecting comprises detecting an optical property of the detection material selected from the group consisting of fluorescence, absorbance, reflectance, translucence, scatter, specific rotation and refractive index.

10. The method of claim 1, wherein the step of heating is conducted in a chamber.

11. The method of claim 1, wherein the detection material is a liquid over a temperature range between the starting temperature and the recorded temperature.

12. The method of claim 1, wherein the detection step is automated.

13. The method of claim 1, wherein the recording step is automated.

14. A system, comprising:
    a controlled area configured to receive a plurality of containers;
    a holding element to provide a centripetal force to the plurality of containers;
    a temperature control element disposed adjacent to the controlled area and configured to provide heat to the controlled area and at least a portion of the plurality of containers;
    a temperature sensor configured to measure a temperature associated with the controlled area;
    at least one detector configured to provide a signal when a detection condition is met, wherein the detection condition comprises a change in a relative position of a test material and a detection material in at least one container of the plurality of containers; and
    a controller configured to provide a control signal to the heating element and alter the temperature associated with the controlled area, receive the signal from the detector, and record the temperature associated with the controlled area at a time the signal is received.

15. The system of claim 14, wherein the temperature control element is configured to cool the controlled area and at least a portion of each container of the plurality of containers.

16. The system of claim 14, wherein the at least one detector is at least one of a photodetector, or a photomultiplier.

17. The system of claim 14, wherein the controller is automated.

18. A method to determine a melting point of a fat material in at least one container comprising the fat material and an aqueous detection material, wherein the aqueous detection material is above the fat material at a starting temperature, wherein the fat material is solid at the starting temperature, wherein the aqueous detection material comprises a fluorescent dye soluble in the aqueous detection material, comprising:

heating the at least one container;

applying a centripetal force to the at least one container, wherein the fat material in the at least one container melts and the centripetal force causes an inversion of the fat material and the aqueous detection material;

detecting a change in the relative position of the fat material and the aqueous detection material, wherein the change is detected by a signal corresponding with the fluorescent dye in the aqueous detection material; and recording a temperature when the fat material and aqueous detection material invert positions, wherein the recorded temperature is the melting point of the fat material.

19. The method of claim 18, wherein the detection step is automated.

20. The method of claim 18, wherein the recording step is automated.

* * * * *